(12) United States Patent
Detalle et al.

(10) Patent No.: US 6,873,419 B2
(45) Date of Patent: Mar. 29, 2005

(54) METHOD AND APPARATUS FOR THREE-DIMENSIONAL COMPOSITIONAL MAPPING OF HETEROGENEOUS MATERIALS

(75) Inventors: Vincent Detalle, Montréal (CA); Marc Dufour, Outremont (CA); Jean-Pierre Monchalin, Montréal (CA); Mohamad Sabsabi, Boucherville (CA); Louis St-Onge, Côte-Saint-Luc (CA)

(73) Assignee: National Research Council of Canada, Ottawa (CA)

( * ) Notice: Subject to any disclaimer, the term of this patent is extended or adjusted under 35 U.S.C. 154(b) by 379 days.

(21) Appl. No.: 09/987,819

(22) Filed: Nov. 16, 2001

(65) Prior Publication Data

US 2003/0095266 A1 May 22, 2003

(51) Int. Cl.[7] .............................................. G01B 9/02
(52) U.S. Cl. ...................................................... 356/479
(58) Field of Search ................................. 356/479, 497, 356/318, 416, 72, 73; 250/281

(56) References Cited

U.S. PATENT DOCUMENTS

| | | | |
|---|---|---|---|
| 4,627,731 A | | 12/1986 | Waters et al. |
| 5,321,501 A | * | 6/1994 | Swanson et al. ............ 356/479 |
| 5,720,894 A | | 2/1998 | Neev et al. |
| 5,877,856 A | * | 3/1999 | Fercher ...................... 356/492 |
| 6,259,530 B1 | * | 7/2001 | Monsallut .................... 356/516 |
| 6,532,068 B2 | * | 3/2003 | Detalle et al. ............... 356/318 |
| 6,643,027 B2 | * | 11/2003 | Gong et al. .................. 356/516 |

OTHER PUBLICATIONS

Günther et al., Spectrochim. Acta Part B, vol. 54, 1999, p. 381.
Kanický et al., Fresenius J. Anal. Chem., vol. 366, 2000, p. 228).
Wong et al., SPIE, vol. 2390, 1995, p. 68.
Kay et al., Int. J. Impact Engng., vol. 19, 1997, p. 739.
Borisov et al., Spectrochim. Acta Part B, vol. 55, 2000, p. 1693.
Lausten and Balling, Appl. Phys. Lett., vol. 79, 2001, p. 884.
Uebbing et al., Spectrochim. Acta Part B, vol. 47, 1992, p. 611.
Rao and Jackson, Meas. Sci. Technol., vol. 7, 1996, p. 981.
Anderson et al., "Depth Profile Studies Using Laser–Induced Plasma Emission Spectrometry", 1369 Applied Spectroscopy, XP000508969, vol. 49, No. 6, Jun. 1995, Society for Applied Spectroscopy, Baltimore, USA.
Borisov et al., "Laser Ablation Inductively Coupled Plasma Mass Spectrometry of Pressed Pellet Surrogates for Pu Materials Disposition", Applied Spectroscopy, XP–001125028, vo. 55, No. 10, 2001, Society for Applied Spectroscopy, Baltimore USA.
Wong et al., "Surface Characterization of Laser Ablated Hard Tissue: A Comparison of Scanning White Light Interferometry and Electron Microscopy", Proceedings of the SPIE, XP009003998, vol. 2390, pp. 68–75, 1995, SPIE Bellingham, VA USA.

* cited by examiner

*Primary Examiner*—Samuel A. Turner
(74) *Attorney, Agent, or Firm*—Freedman & Associates

(57) ABSTRACT

Laser ablation combined with spectrometric analysis is a good tool for determining the composition of heterogeneous materials. By measuring the depth of an ablation crater at a target of a heterogeneous material, it is possible to generate a compositional profile as a function of the depth. It is also possible to generate a 3 dimensional profile by depth profiling of a plurality of craters. The depth measurement is conducted in situ and in real time so that the evolution of composition as a function of the depth can be measured. An interferometric technique with a short coherence length light is one of the preferred embodiments for measuring the depth in situ and in real time.

24 Claims, 6 Drawing Sheets

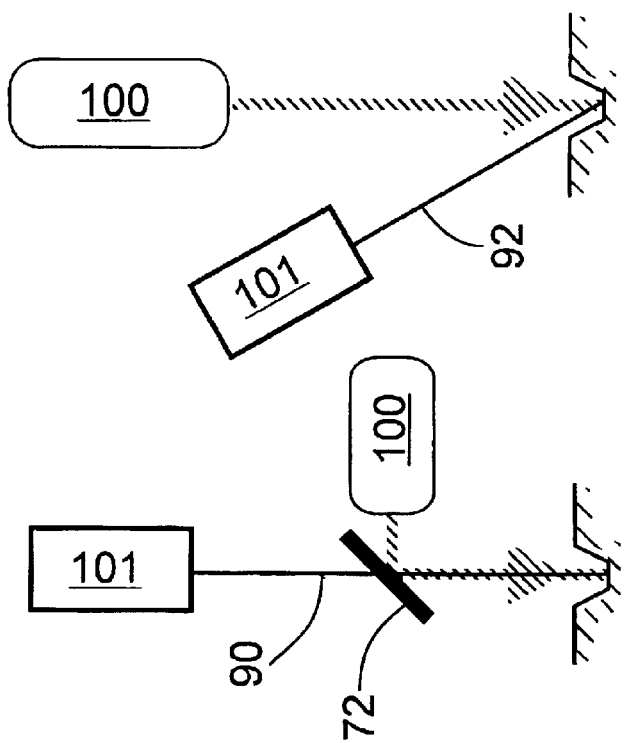
Fig. 3d
Fig. 3c
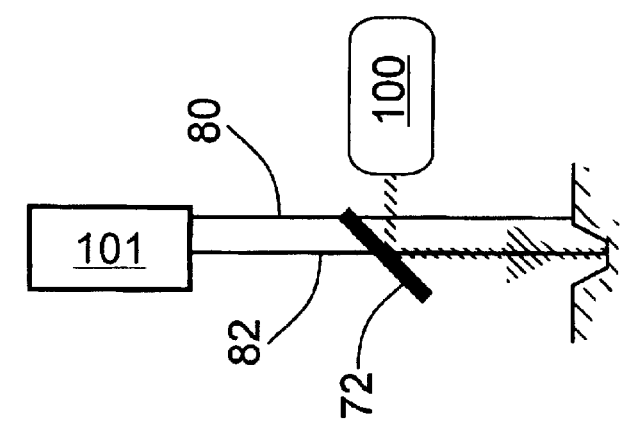
Fig. 3b
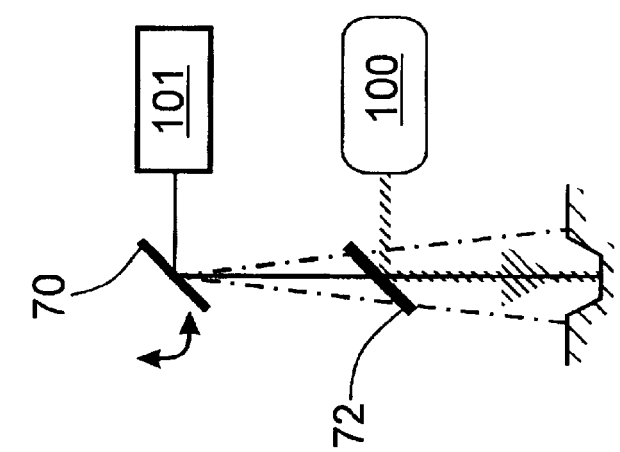
Fig. 3a

METHOD AND APPARATUS FOR THREE-DIMENSIONAL COMPOSITIONAL MAPPING OF HETEROGENEOUS MATERIALS

FIELD OF THE INVENTION

This invention relates to optical instrumentation, and more particularly to a method and apparatus for three-dimensional compositional mapping of heterogeneous materials by laser-ablative sampling combined with optical sensing of sampling positions.

BACKGROUND OF THE INVENTION

Materials in different stages of transformation from raw material to finished product often present a heterogeneous elemental composition. In particular, an object'surface may be functionalized using one or several layers of varying composition or physical properties. There is a growing need in industry, namely in the context of process development and process control, for at-site high-throughput methods that can reveal the distribution of one or several elements along one or more spatial dimensions.

Classical analytical techniques have largely focused on the determination of bulk compositions, and a few can provide spatially-resolved information. Typically, the material is dissolved and introduced as a solution in the analytical instrument, yielding only average elemental concentrations. Techniques based on an arc/spark do allow direct solid sampling (of electrically conducting materials) without a digestion step. However, they do not possess the capability to provide accurate spatially resolved analyses (Güther et al., Spectrochim Acta Part B, vol. 54, 1999, p. 381).

Other techniques, such as Auger or X-ray photoelectron spectrometry, allow the study of surface chemistry one the atomic scale, and can also provide depth-resolved analyses when removing successive layers of material through ion bombardment. In secondary ion mass spectrometry (SIMS), such a bombardment is inherent to the measurement process as the composition at different depths is inferred from the nature of bombardment-induced secondary ions. In order to avoid particle scattering in the gas phase, these and other techniques with similar attributes require working in ultra-high vacuum conditions. Glow-discharge methods coupled to optical emission spectrometry or mass spectrometry have also been used to probe coatings, over thicknesses ranging from 0.01 $\mu$m to 50 $\mu$m. Measurement time is typically 15 minutes and depth resolution is around 100 nm, while lateral resolution is poor.

The methods described above all involve some preparation of the sample, are time consuming, and require sophisticated and expensive instrumentation. Moreover, the sample shape and size is limited by the sample chamber configuration. Some also suffer from limited sensitivity or spatial resolution. For these reasons, they do not meet the industrial needs for at-site high-throughput compositional mapping of heterogeneous materials.

Laser radiation, on the other hand, possesses several attributes that make it particularly well suited for the task of analysing heterogeneous materials. In so-called laser ablation, a focused laser pulse provides locally a very large power density that transforms a small amount of solid material directly into a vapor plume suitable for further analysis. The possibility of concentrating laser radiation on a very small surface enables the sampling and analysis of heterogeneous materials with very good lateral resolution (down to a few micrometers). The separate analysis of successive laser ablation events at a same position on the solid material also enables a depth-resolved analysis, the depth reached by each laser shot ranging from tens of nanometers to tens of micrometers depending on the laser characteristics and material type.

Laser ablation (LA) in itself is not sufficient for compositional analysis. Two main schemes exist that can complement its role of direct solid sampling: i) the luminous plasma formed above the specimen surface concomitantly with the ablation event is analysed through optical emission spectrometry (OES), in a technique known as laser-induced plasma spectroscopy (LIPS), or (ii) the sampled matter is carried in a gas stream to an auxiliary inductively-coupled plasma (ICP) and detected through optical emission or mass spectrometry (in so-called hyphenated techniques known as LA-ICP-OES and LA-ICP-MS respectively). The first scheme (LIPS) is rapid, involves relatively simple instrumentation and analytical procedures, and is relatively inexpensive. Moreover, contrary to the second scheme which requires the sample to be enclosed in a laser ablation cell, LIPS can be applied to samples of any size or shape, and can function at a distance. Therefore, LIPS is the most amenable to at-site, in-situ, and high-throughput compositional mapping of heterogeneous materials.

Any compositional mapping of a solid material requires not only knowledge of the composition at a given analysis site but also an accurate knowledge of the site location in three-dimensional space. Knowledge of the laser impact site on the sample in the two dimensions transverse to the laser beam is easily gained by a precise and user-controlled steering of either the sample or the laser beam in these dimensions. Determining the position in the other direction, for example the distance between the bottom of the laser-produced crater and the sample surface beside the crater, is more difficult.

Following one or a sequence of laser ablation events, the sample can be taken to another instrument with which the crater depth will be determined. Such an instrument can be of a mechanical or optical type. In the first case, a fine point is moved across the surface of the sample, and the crater profile and depth is determined from the displacement of the point. For example, Kanický et al. (Fresenius J. Anal. Chem., vol. 366, 2000, p. 228) have used such a mechanical profilometer to assess the shape and depth of craters in the context of depth-profile analysis of tin-coated glass by LA-ICP-OES. In the second case, the instrument can be based on confocal microscopy, laser triangulation, or interferometry using a short coherence length light source (also called white light interferometry or optical coherence tomography). Wong et al. (SPIE, vol. 2390, 1995, p. 68) have used white light interferometry for the study of laser-ablation craters in bone in the context of laser treatment, not compositional analysis. Kay et al. (Int. J. Impact Engng., vol. 19, 1997, p. 739) have also used this technique for the characterization of impact (not laser-produced) craters. Borisov et al. (Spectrochim. Acta Part B, vol. 55, 2000, p. 1693) used a white-light interferometric microscope to study the parameters of laser-produced craters in the context of LA-ICP-MS analysis of a glass sample.

In order to establish a detailed depth profile, one needs to perform several compositional measurements at different depths in the material. To avoid repeatedly carrying the sample to a separate instrument for the determination of depth, and the subsequent need for precise positioning of the sample in the laser ablation apparatus, one can resort to a preestablished calibration of the crater depth on the basis of the cumulative number of laser shots. In this way, the compositional analysis for a given laser shot is made to correspond to a given depth. In cases where the sample comprises a coating and a substrate, both having significantly different ablation rates (ablated depth per laser shot), different calibrations can be used for the coating and substrate, and an interpolation can be used for the interface region. This procedure assumes that the ablation rate is the same for the study sample and the calibration sample, which in particular requires sufficient stability of the laser pulse energy and beam radial profile. However, this approach is limited to relatively simple cases. It would not be applicable to samples for which the ablation rate varies in a continuous manner as a function of depth, or to complex multilayer samples.

An example of such a problematic case is the compositional mapping of pharmaceutical tablets by LIPS. The core of pharmaceutical tablets consists of a compacted blend of different components (active agent, lubricant, inactive excipient, etc.) originally in powder form, and may be coated with a film (typically containing titanium dioxide and other ingredients). U.S. Pat. No. 5,781,289 Jul. 14, 1998 by Sabsabi and Bussiere describes the use of LIPS for the analysis of preselected components in homogeneous pharmaceutical compositions, for example for the quantification of the average active agent concentration in tablets. Although such a spatially-averaged analysis by LIPS can find several uses in pharmaceutical process development and control, a mapping capability would prove useful for another set of problems: (i) assessment of powder blend uniformity by the mapping in tablets of the drug, lubricant or other components, or (ii) evaluation of coating homogeneity and thickness across the surface of the tablet. In the latter case, a depth-profiling capability is required. However, because of the particular laser-matter interaction that occurs in tablets and of the granular nature of tablets, the corresponding ablation rate is usually very large compared to that in a metal for instance. Whereas on a metal tens of nanometers are ablated per laser shot, 10–15 $\mu$m can be ablated per pulse in a tablet coating and up to 50–100 $\mu$m per shot in the core of tablets. As a result, the aspect ratio (depth-to-diameter ratio) of the laser-produced crater can grow very large, thus significantly modifying the ablation rate at each successive shot (because of a decreasing laser energy density on the crater surface due to an increasing exposed surface, or because of increasing confinement of the ablated matter and of plasma in the crater). A depth calibration in this case would not be possible. The same would be true if instead of using LIPS, the analysis proceeded through the transfer of the ablated matter to an auxiliary discharge and detection system (as in LA-ICP-OES or LA-ICP-MS). The same would also be true of any other analysis based on direct solid sampling by laser ablation where the ablation rate varies continuously as a function of depth, or where the multilayer structure of the sample is so complex as to preclude any calibration.

Combining laser ablative sampling and optical sensing of the sampling position in a single integrated apparatus would provide a means of determining in real time the depth of laser-produced craters for each laser shot if desired, thus eliminating the need for depth calibration. U.S. Pat. No. 6,259,530 B1 Jul. 10, 2001 by Monsallut describes a method and device, based on optical heterodyne interferometry, for measuring the depth of craters obtained by the bombardment, with a beam of primary ions, of a sample placed in the analysis chamber of a physico-chemical analyzer, such as a SIMS instrument. This invention relates to depth-profile analysis by ion-based techniques in high-vacuum chambers. It does not feature an integrated optical system performing both functions of laser-ablative sampling and crater-depth evaluation. Moreover, this method requires the optical paths to follow an incident direction inclined in relation to the surface of the sample (thus freeing the space needed for the circulation of secondary ions extracted from the sample). Consequently, this configuration would not be adequate for the characterization of craters with large aspect ratio, since shading might occur.

Lausten and Balling (Appl. Phys. Lett., vol. 79, 2001, p. 884) describe a method for the real-time measurement of crater depth during ablation with ultrashort laser pulses, in the context of laser micromachining or laser surgery. The method is based on the time-gated imaging of the backscattered radiation from the ablation region. The crater shape is deduced from the time-of-flight of light to and from the object. For this reason, shorter pulses will provide better spatial resolution. However, even for a pulse as short as 100 fs (i.e. $10^{-13}$ s), the depth resolution is only about 15 $\mu$m, which would not be suitable for many depth-profile analysis applications. The method becomes wholly inapplicable with ns-duration ($10^{-9}$ s) laser pulses widely used for LIPS, LA-ICP-OES or LA-ICP-MS. Therefore, there is a need to provide an optical tool for the non-contact, in-situ and real-time measurement of the depth of laser-produced craters, for each laser shot or at any shot number interval desired. The in situ and real time measurement of depth eliminates the need to periodically characterize the crater depth in another separately-located instrument, or to rely on a calibration of depth (based on cumulative shot number) for a given material, or finally to resort to an interpolation of such calibrations for describing the interface between two materials.

SUMMARY OF THE INVENTION

In one aspect, the invention is to provide a rapid and accurate three-dimensional compositional mapping of heterogeneous materials, which in particular may feature large changes in composition and physical properties as a function of depth. Accordingly, this invention consists in a new method and apparatus for simultaneously measuring the composition of ablated matter and the crater depth corresponding to a given laser ablation event, thus providing a more rapid and accurate compositional depth profile than achievable by current methods and instrumentation.

In accordance with another aspect, the invention is directed to a method of compositional analysis of a heterogeneous material of one or more components. The method comprises steps of: (a) directing a pulse of laser radiation at a target of the heterogeneous material to ablate an amount thereof, and to form an ablation crater having a depth and (b) determining the concentration of one or more selected components in the heterogeneous material ablated from the target. The method further includes steps of (c) measuring the depth of the ablation crater, and (d) determining in situ and in real time a composition of the heterogeneous material at the depth.

In another aspect, the invention is directed to an apparatus for compositional analysis of a heterogeneous material of one or more components. The apparatus comprises a laser source for producing an ablation beam of laser pulses of sufficient fluence to ablate an amount of the heterogeneous material from a target under study and thereby to form an ablation crater of a depth. The apparatus further includes a spectrometric device for detecting and determining the concentration of one or more selected components in the heterogeneous material ablated from the target and an optical device for measuring in situ and in real time the depth of the ablation crater.

In yet another aspect, the apparatus includes the optical or mass spectrometric device for a spectrochemical analysis. The optical spectrometric analysis analyzes light emitted by the plasma produced above the target concomitantly with the laser ablative event or following the transport of the ablated material to an auxiliary plasma discharge (for example an inductively coupled plasma) where the material is excited to emit light. The mass spectrometric analysis detects and determines the concentration of one or many selected components in the material ablated from the target, following its transport to said auxiliary plasma discharge, from which it is extracted in ionized form.

In a yet further aspect, the invention includes an optical device for measuring the depth of the ablation crater. The optical device may be a confocal microscopy device, a laser triangulation device, or an interferometer using a short coherence length light source.

The radial distribution of energy in the laser beam may be tailored in such a way as to provide a substantially uniform beam, thus producing a crater with flat bottom and steep walls, which generally leads to an improvement in depth resolution.

DESCRIPTION OF THE DRAWINGS

The objects, features and advantages of the present invention will become apparent from the following detailed description of the invention in conjunction with the drawings in which:

FIGS. 3a to 3d show different configurations of the laser ablation beam and depth measurement beam.

DETAILED DESCRIPTION OF THE PREFERRED EMBODIMENTS

Figure 1:
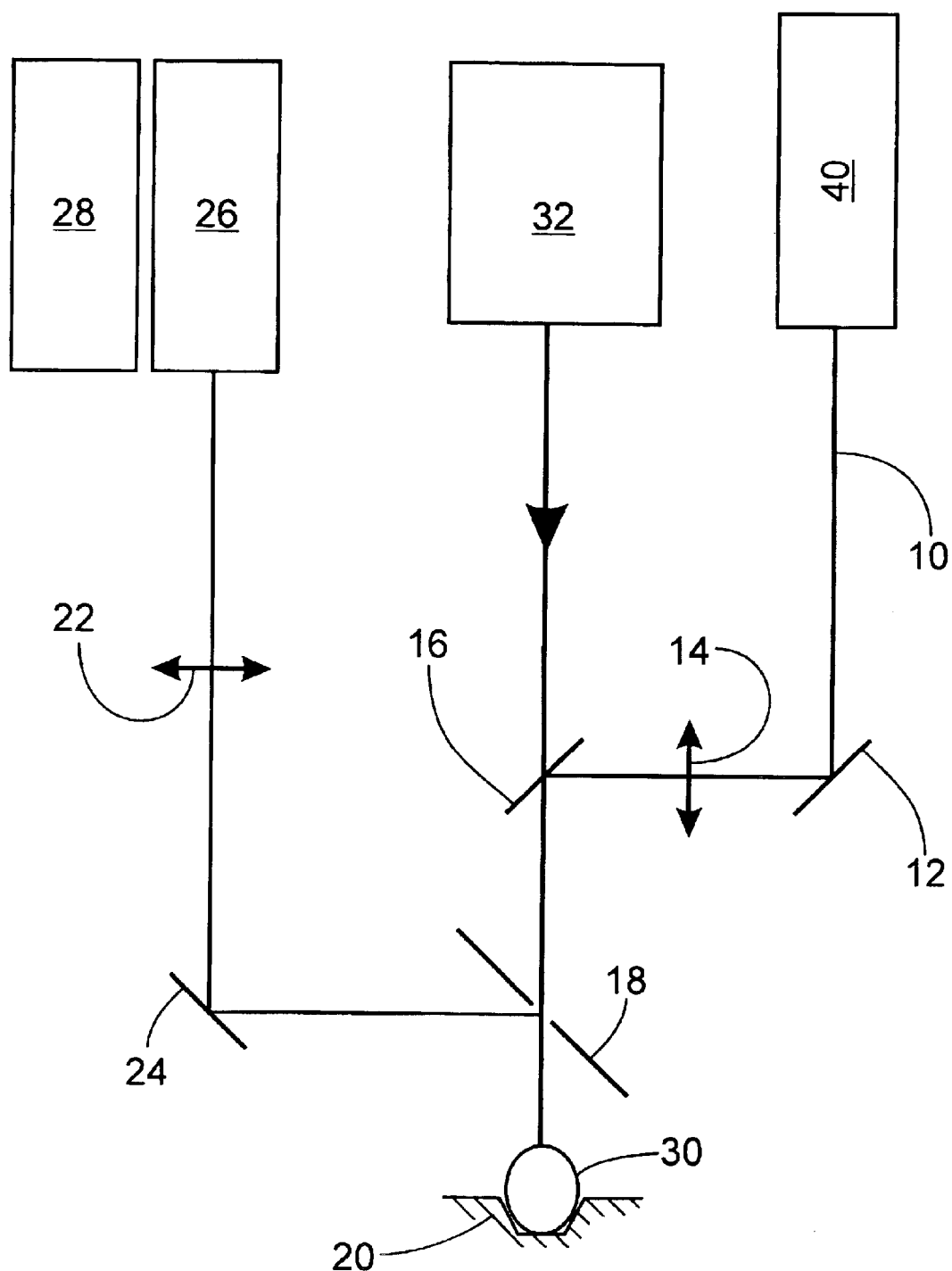
FIG. 1 is an overall block diagram of the invention according to a preferred embodiment.

In accordance with the principles of the invention, the functions of laser ablative sampling and optical sensing of the sampling position are integrated in a single optical apparatus.

In addition to these two functions, a complete analytical apparatus must also include the means for analysing the composition of the ablated matter. In the LIPS technique, the luminous plasma formed above the specimen surface concomitantly with the ablation event is analysed through optical emission spectrometry. Different elements present in the sample are identified by the emission of characteristic spectral lines at well-known wavelengths. Furthermore, their concentration can be deduced from the spectral line intensity, following calibration using certified standard materials. In general, time gating of the detection device is used so as to eliminate the very intense and less useful continuous and ionic emission of the first instants of the laser-produced plasma. In other techniques, the sample is enclosed in an ablation chamber comprising a window through which the ablating laser can be focused. After extinction of the laser-produced plasma, the ablated and atomized matter recondenses in aerosol form and is transported in a gas stream (usually argon) toward an auxiliary continuous plasma device, usually an inductively-coupled plasma (ICP). The ablated material can also be introduced directly into the auxiliary plasma device, for example a microwave-induced plasma device (Uebbing et al., Spectrochim. Acta Part B, vol. 47, 1992, p. 611), which connects directly with the laser ablation chamber. The aerosol is again atomized and ionized in the auxiliary plasma device, with some of the atoms and ions being brought to excited states. The detection of excited atoms or ions by optical emission spectroscopy (as in LIPS) can then be used to identify and quantify the elements present. Alternatively, the quantitative elemental analysis can be performed following the extraction and mass-separation of ions by electrostatic means, using a mass spectrometer. Although in the present invention the ablated matter may be introduced in such a way into an auxiliary plasma to perform the spectrochemical analysis, the preferred embodiments described below rather integrate the LIPS scheme. It allows more flexibility in terms of sample shape and size or even movement since the sample does not have to be enclosed in an ablation chamber.

The depth at which each measurement is made has to be evaluated in-situ and in real time. Depth evaluation can be based on confocal microscopy, laser triangulation or interferometry using a short coherence length light source (also called white light interferometry or optical coherence tomography). In confocal microscopy, light is sent through a pinhole and the light collected through the same pinhole after reflection by the object is monitored. The surface location is determined by noting that the collected light is at maximum when the image of the pinhole is at focus on the surface. In laser triangulation, the light spot at the surface of the object is viewed by a linear camera along a direction making an angle with the illumination axis. The position of the spot on the linear camera is dependent upon the distance of the surface from the device, which allows monitoring the surface location. In interferometry with a short coherence length source, a maximum interference signal is observed when the path length along the arm going to the object is equal to that of a reference arm whose length is varied. This variation being calibrated, this technique also allows monitoring the surface location. The following embodiments show how the depth evaluation can be accomplished by using interferometry with a short coherence length source.

The material to be analysed may be opaque or partly transparent. As a result of the high temperature generated by the focused laser beam, a small amount of the material is ablated, vaporized and ionized, its atoms and ions being brought to excited states, thus allowing species in the plasma to be identified by spectrally and temporally resolving the spark light emission (in LIPS). The optical emission is analysed with a spectrometer and the spectrum is detected through appropriate optics by a gated photodiode array detector, an intensified CCD camera, or by an array of photomultipliers each individually positioned to detect an emission line representative of a given element.

To perform a reliable depth profile analysis, it is important to ensure a controlled and reproducible ablation rate and a well-characterized ablation volume. The ablation has to be the same for each shot in terms of radial distribution of the ablated depth. In order to obtain this result, the spatial characteristics of the laser beam have to be controlled and the laser needs to be stable from shot to shot. In particular, to achieve a good depth resolution, all parts of the laser beam throughout its cross-section should sample the material at approximately the same depth. This condition is difficult to satisfy with a near-Gaussian laser beam, which produces cone-shaped craters. Inevitably, for any given shot (except the first), the laser will sample material from different depths along the crater surface. Therefore, one may want to tailor the radial distribution of energy in the laser beam (for instance by using a diaphragm to select only a homogenous part of the beam) so as to produce a crater with flat bottom and steep walls.

One of the preferred embodiments is shown in FIG. 1. In the Figure, the laser beam 10 of sufficient fluence (spatial energy density or energy per unit surface) for ablation is reflected by a mirror 12 through focusing optics 14 and is reflected by a dichroic plate 16. The laser beam goes further through a pierced mirror 18 to a target 20. The focusing optics may also be placed after the dichroic plate.

With the aid of a lens 22 and the pierced mirror 18, a reduced image of the plasma is created at the entrance slit of the spectrometer 26, which is connected to a data processing unit 28. Another mirror 24 may be provided to redirect the light from the plasma. This configuration allows efficient collection of the light emitted by the plasma 30 along the axis of the plasma plume using a pierced mirror. The optical emission from the plasma is spectrally analyzed using typically a grating spectrometer equipped with a gated detector such as an intensified photodiode array detector, CCD camera, or an array of photomultipliers each individually positioned in the focal plane to detect, simultaneously and during a specified time period, a number of emission lines representative of the different elements in the material to be analyzed. Standard techniques are used to properly synchronize the laser and detector so as to collect the emission signal during the time window providing the best signal-to-noise ratio, while a fast computer evaluates the measured spectra and calculates the element concentrations via calibration procedures which are well known to spectroscopists.

FIG. 1 also shows how the crater depth evaluator, namely an interferometer 32 with a short coherence length source, is an integral part of the apparatus of the present invention. In this embodiment, the optical path of the interferometer leading to and from the sample passes through the dichroic plate 16 and pierced mirror 18.

Figure 2A:
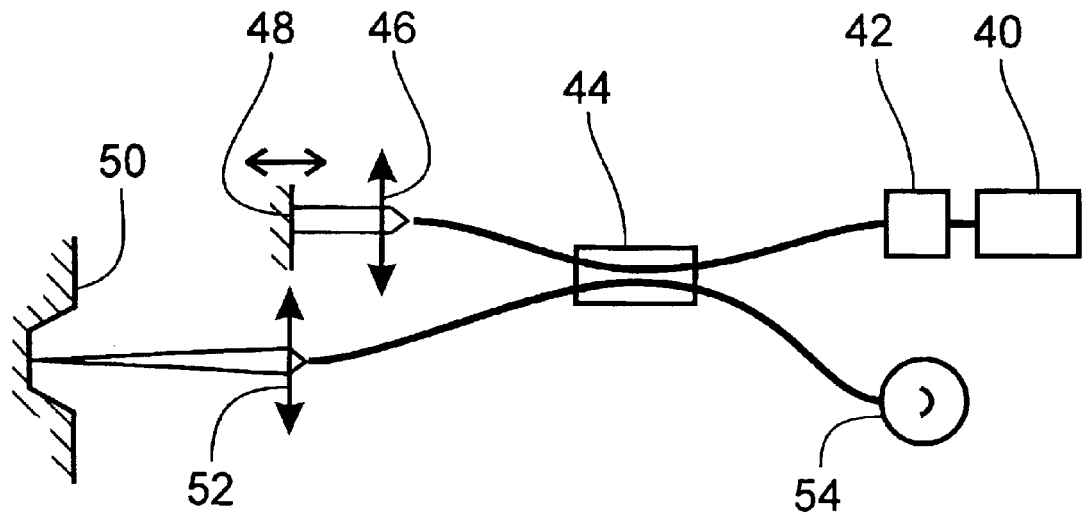
FIGS. 2a and 2b show two possible embodiments of the invention where the depth measuring function is realized by interferometry with a short coherence length source.

The interferometer depicted in FIG. 1 may take several forms. FIG. 2a shows an embodiment that allows a depth measurement at one point on the sample. The depth evaluation function is realized by a two-wave Michelson interferometer made of single mode optical fibers. A supraluminescent diode 40 giving a bandwidth of typically 20 nm is used as light source. This diode is followed by an optical isolator 42 to prevent feedback from any interface and from the surface of the object of affecting its operation. The beam is then fed through a splitter/mixer 44, which is a 50–50% bi-directional coupler. The reference arm length is varied by collimating the beam with a lens 46 and mounting the mirror 48 (or a retroreflector) on a translation slide. In the arm going to the sample 50, the beam emerging from the fiber is focused by a lens 52 and directed onto the sample surface. Laser beam reflected back from the sample and the mirror is combined at the splitter/mixer 44 and interference is measured by a detector 54, deriving the depth of the crater on the sample.

Figure 2B:
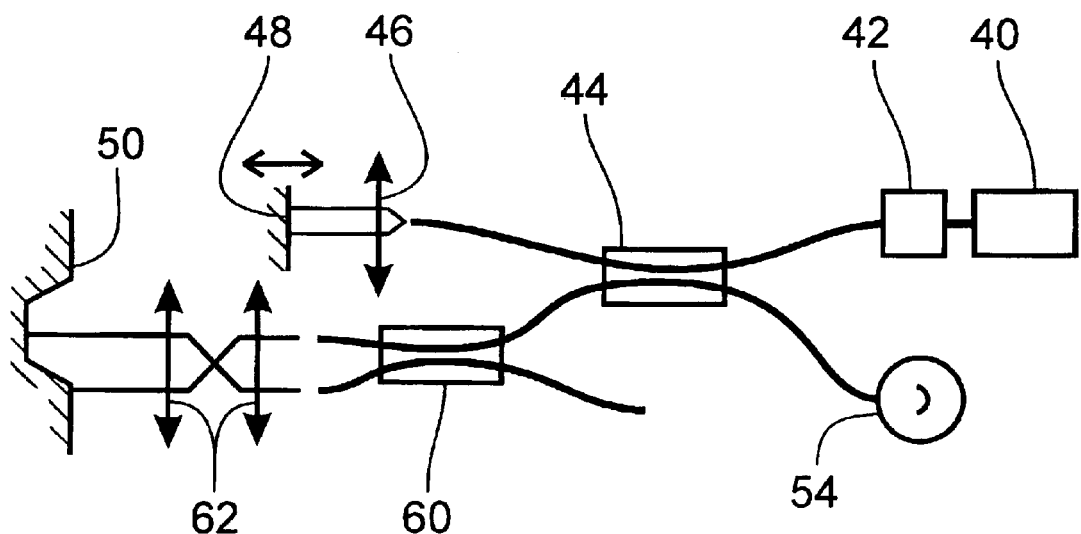

The embodiment shown in FIG. 2b enables depth measurements at two points, for example one inside the crater at its center and the other one outside the crater in a region unaffected by ablation and residual debris. A second 50–50% bi-directional coupler 60 is used in the arm going to the sample to give two secondary light sources that are separated by a given distance (one arm of this bi-directional coupler is unused). A telecentric optical system 62 made of two lenses is then used to focus them on the sample, at two different measurement locations. The two secondary sources given by the second 50–50% coupler are not in the same plane so that the two interferometric signals are conveniently separated before the start of any ablation.

Other interferometer configurations than those shown in FIGS. 2a and 2b are possible, for example the so-called dual-beam configuration (Waters and Fernald, U.S. Pat. No. 4,627,731 Dec. 9, 1986) or dual-interferometer configuration (Rao and Jackson, Meas. Sci. Technol., vol. 7, 1996, p. 981); they are intended to be comprehended within the scope of the appended claims.

In order to determine the ablation crater profile, or simply the crater depth, several approaches are possible. One preferred embodiment, depicted in FIG. 3a, consists in using an interferometer that performs a one-point measurement (as in FIG. 2a) and a rotating slide or galvanometer 70 to reflect the interferometer beam, so as to scan a line across the crater. The interferometer beam and ablating laser beam are superimposed using a dichroic plate 72 and are substantially colinear. Assuming that the reference arm scan in the interferometer is much faster than the scan across the crater, depth information is obtained for each position along a line across the crater from the signal observed at zero path length difference on the interferometer detector. Such a scan can be repeated in order to record the evolution of crater profile as a function of time, simultaneously with a succession of laser ablation events. Instead of using a rotating slide or galvanometer, a linear measurement scan on the sample surface may be realized by translating the interferometer source along a line transverse to the beam.

In order to measure the depth at several points within a plane covering the whole crater area instead of scanning just a line, one may perform several such line scans side-by-side by moving the sample or the beam of the optical depth evaluator in a direction perpendicular to a line scan.

A crater depth evaluation may also be performed using an interferometer that allows a two-point measurement (as the one depicted in FIG. 2b). Such an approach is illustrated in FIG. 3b, where two parallel measurement beams 80 and 82 exiting the interferometer perform two depth measurements, one inside the crater at its center and the other one outside the crater in a region unaffected by ablation and residual debris. The crater depth is then defined as the distance between the two measurement points in the longitudinal direction. In this case, no scanning across the crater is necessary.

When only the position of the crater bottom is sought, it is also possible to perform a one-point non-scanning measurement, as depicted in FIG. 3c. As the ablating laser repeatedly digs into the sample, the evolution of crater depth can be determined using a measurement beam 90 from the interferometer. The ablating laser and measurement beam are colinear. This approach will give better results (in terms of accuracy) when large depth variations occur with each ablating laser shot.

Yet another possible approach is the one depicted in FIG. 3d, where the interferometer measurement beam 92 is not colinear but at an angle with the ablating laser beam, thus eliminating the need for a dichroic plate to superimpose the two beams. With this approach, one needs to be careful that the angle relative to normal is not so large as to allow shading of the interferometer beam by the crater rim, which would prevent a depth measurement at the crater bottom (especially with craters of large aspect ratio). Variations on the configuration of FIG. 3d are possible, including a scanning one-point measurement (similar to FIG. 3a), or a fixed two-point measurement (similar to FIG. 3b). In all cases, when determining the evolution of crater depth, data processing is needed to account for the angle of the measurement beam relative to normal.

For all the embodiments described above where a dichroic plate is used to combine the interferometer and laser beams, another variation is possible where instead of providing a dichroic plate that reflects the laser beam and transmits the interferometer beam, one provides a dichroic plate that reflects the interferometer beam and transmits the laser beam. In this case, the scanning approach of FIG. 3a could be realized more simply by rotating the dichroic plate itself.

In tests conducted to validate this invention, the composition of multi-component pharmaceutical tablets having a film coating was analysed by LIPS as a function of the depth, as measured in-situ and in real time by interferometry with a short coherence length source. The core of the tablets contained 10% (by weight) of an active agent bearing a chlorine atom which could be used as a tracer element for the LIPS analysis. The film coating (less than 100 $\mu$m thick) contained titanium oxide. The ablation laser was a Nd:YAG solid state laser (emitting at 1064 nm) with a pulse duration of 6 ns (full width at half maximum). The laser energy was 90 mJ per pulse and the repetition rate was 1 s$^{-1}$. The laser beam was focused to a spot size of approx. 600 $\mu$m on the tablet surface. The light emission from the laser-produced plasma was analysed by a 0.66 m spectrograph of the Czerny-Turner type provided with a 1200 grooves/mm holographic grating. The dispersed light was detected by an intensified photo-diode array at the exit port of the spectrograph. The grating was positioned so that a 20-nm wide spectrum centered on 840 mm could be recorded. The gated detector was synchronized with the laser pulse so as to integrate light during the period from 1 to 3 $\mu$s after the pulse. The in-situ depth evaluation was realized using an interferometer of the type shown in FIG. 2a, provided with a supra-luminescent diode operating at 1310 mm. A scanning one-point measurement was performed (as depicted in FIG. 3a) so as to obtain line scans across the craters. A line scan included 100 depth measurements on a distance of 3 mm and lasted 1 second, so that a line scan was performed for each laser shot, thus providing real-time monitoring of the depth of the crater at which analysis is performed.

Figure 4:
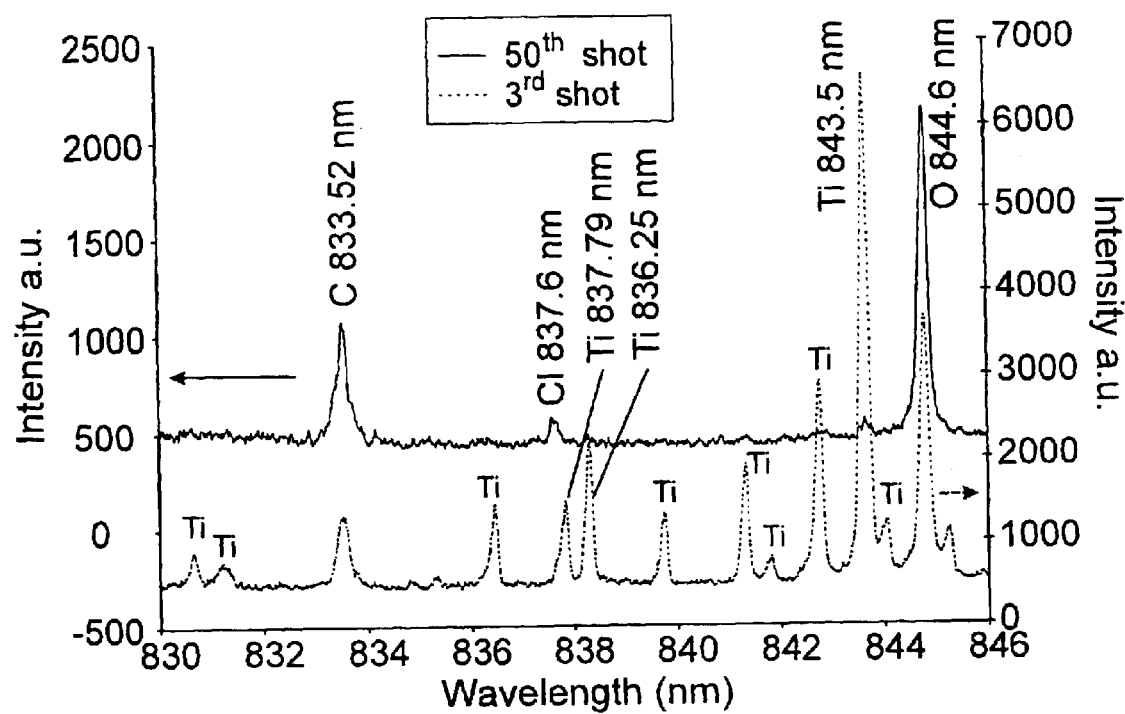
FIG. 4 shows two different emission spectra, one characteristic of the tablet coating and one characteristic of the tablet core.

Two hundred laser shots were fired at the same position on a tablet in order to obtain a depth profile. FIG. 4 shows two different emission spectra, one obtained at the 3$^{rd}$ shot at a depth still substantially within the tablet coating, and the other obtained at the 50$^{th}$ shot, which is well within the tablet core. In the first case, the presence of titanium oxide in the coating contributes many prominent titanium lines. Emission from carbon and oxygen is also observed since organic compounds are present in the coating. However, the chlorine line at 837.60 nm is barely noticeable (on the wing of the Ti 837.79 nm line) because the tablet core has not yet been penetrated significantly. After 50 shots, the reverse is observed. Titanium lines have virtually disappeared, while the chlorine line is readily observed. A weak titanium signal (here seen at 843.5 nm) can persist even when the center of the beam has long penetrated the core of the tablet because the periphery of the laser beam can interact with the walls of the crater (including part of the coating at the surface).

Figure 5:
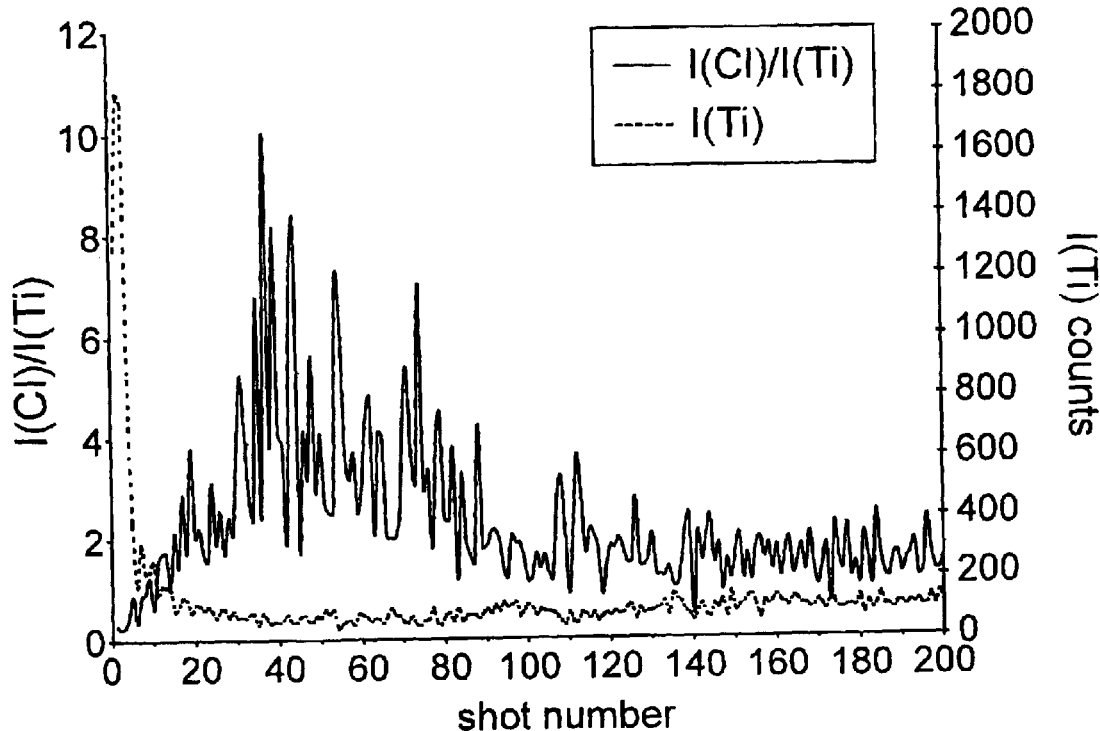
FIG. 5 shows the evolution of spectral line intensities obtained by LIPS as a function of the number of laser shots.

FIG. 5 shows the fill evolution of spectral line intensities for the whole 200-shot series. It was difficult to exploit directly the chlorine line because of interference by the titanium line at 837.79 nm. The dashed line rather shows the emission intensity at 838.25 nm, which is the sum of the titanium signal at this wavelength and of a background signal (see FIG. 4). One sees readily that the titanium signal drops rapidly within the first 6 shots on the surface, indicating complete penetration through the coating. Beyond the 6$^{th}$ shot, there is a slower decay up to the 20$^{th}$ shot, after which the intensity is constant at approximately 100 counts, this signal being attributable almost entirely to the background emission. In order to further characterize the transition between the coating and the core, FIG. 5 shows the ratio of raw chlorine intensity to raw titanium intensity, i.e. the ratio of the total intensity (line plus background) at 837.6 nm to the total intensity at 838.25 mm. The raw intensities are used so that, even when there is no titanium line, the denominator is not zero because of background emission. One sees that the Cl/Ti ratio steadily increases starting from the 4$^{th}$ or 5$^{th}$ shot up to approximately the 20$^{th}$ shot where a plateau is reached. The large spikes observed are attributable to variations of chlorine content in the ablated matter, clearly illustrating the heterogeneous nature of the tablet core, where only 10% of the compacted powder contains chlorine. After about 80 shots, the Cl/Ti ratio decreases because of changes in laser-target interaction and of plasma confinement attributable to the larger aspect ratio of the crater. The Cl/Ti ratio then settles at a value between 1 and 2. In the absence of chlorine and titanium lines, the intensity ratio would correspond to a ratio of background signals at very close wavelengths, which would be equal to 1. In fact, the chlorine is still detected after 200 shots, thus giving a ratio larger than 1.

Figure 6:
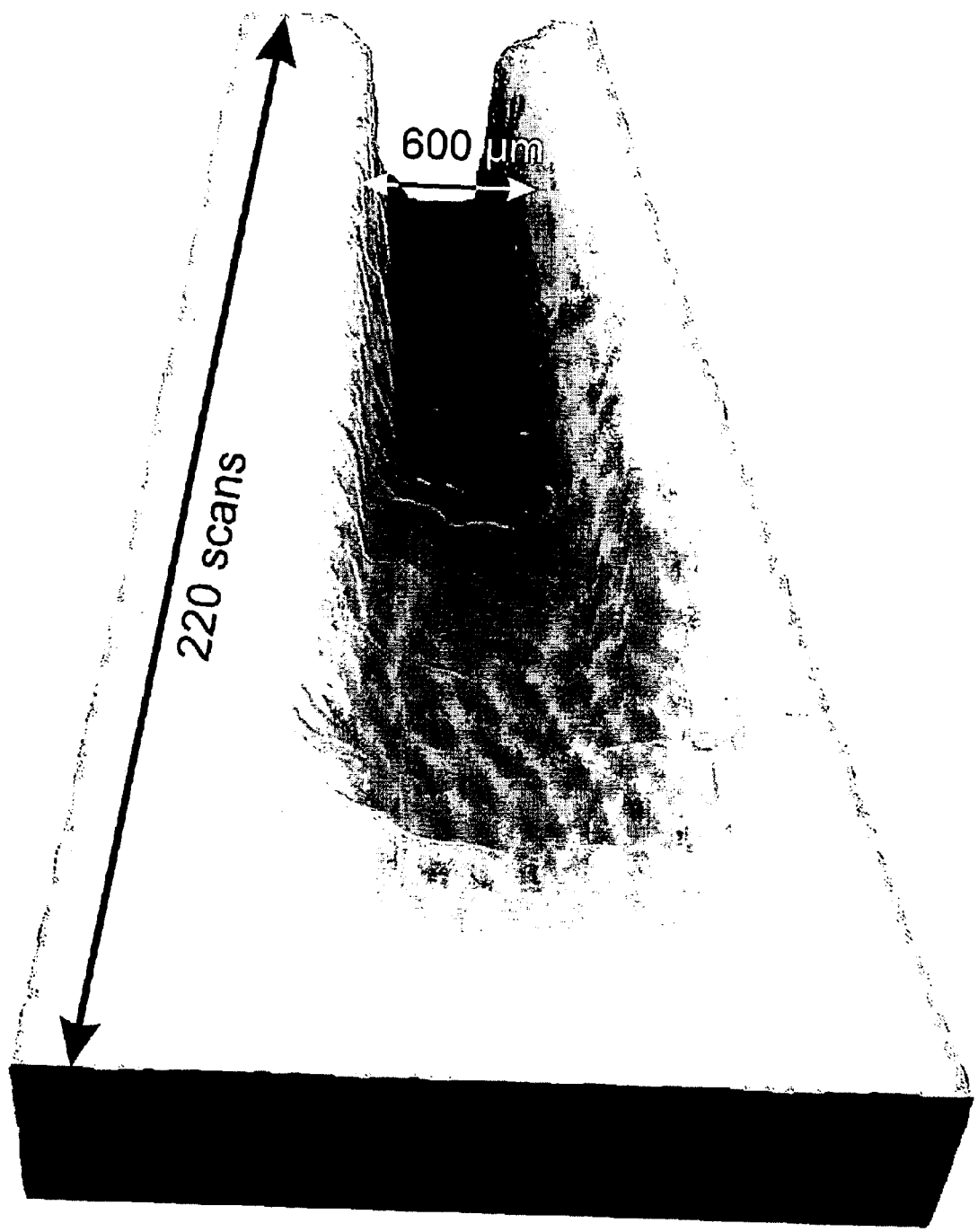
FIG. 6 shows the evolution of the crater profile obtained with 220 successive line scans of the depth measurement beam. The 200 ablation laser shots occurred from the $10^{th}$ to the $210^{th}$ line scan.

FIG. 6 shows the evolution of the cater profile obtained with 220 successive line scans of the depth measurement beam. The 200 ablation laser shots occurred from the 10$^{th}$ to the 210$^{th}$ line scan. The crater depth is seen to steadily increase with the number of laser shots. Near the end, the crater is found to have rather steep walls and the crater width is approximately 600 $\mu$m, corresponding to the laser spot size.

Figure 7:
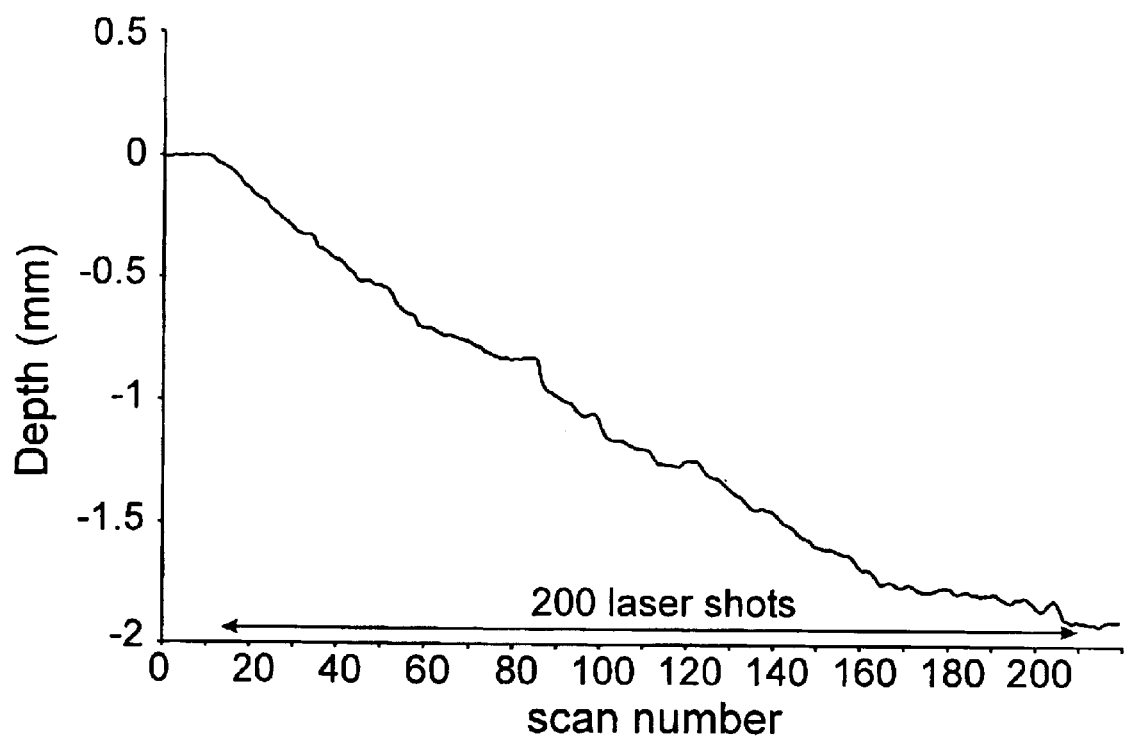
FIG. 7 shows the evolution of crater depth as a function of the scan number. The 200 ablation laser shots occurred from the $10^{th}$ to the $210^{th}$ line scan of the depth measurement beam.

FIG. 7 shows part of the data of FIG. 6, i.e. the evolution with scan number of the depth at the bottom of the crater. The depth starts to increase at the 10$^{th}$ scan when the first laser shot is fired. The final depth (at the 210$^{th}$ scan) is approximately 1.9 mm, corresponding to a crater aspect ratio of approximately 3 (i.e. 1.9/0.6). Some discontinuities are observed in the profile, for instance between the 80$^{th}$ and 90$^{th}$ scan, indicating that large powder particles are sometimes removed suddenly from the target. Another feature of the depth profile shown in FIG. 7 is the change in ablation regime at approximately the 160$^{th}$ scan (i.e. 150$^{th}$ laser shot), where the ablation rate (depth ablated per laser shot) is seen to decrease. This shows that a depth calibration based on the number of shots would not be applicable to the whole sequence of shots in this case, thus illustrating the usefulness of the preset invention in providing an in-situ and real-time measurement of the actual depth reached by each ablating laser shot.

Figure 8:
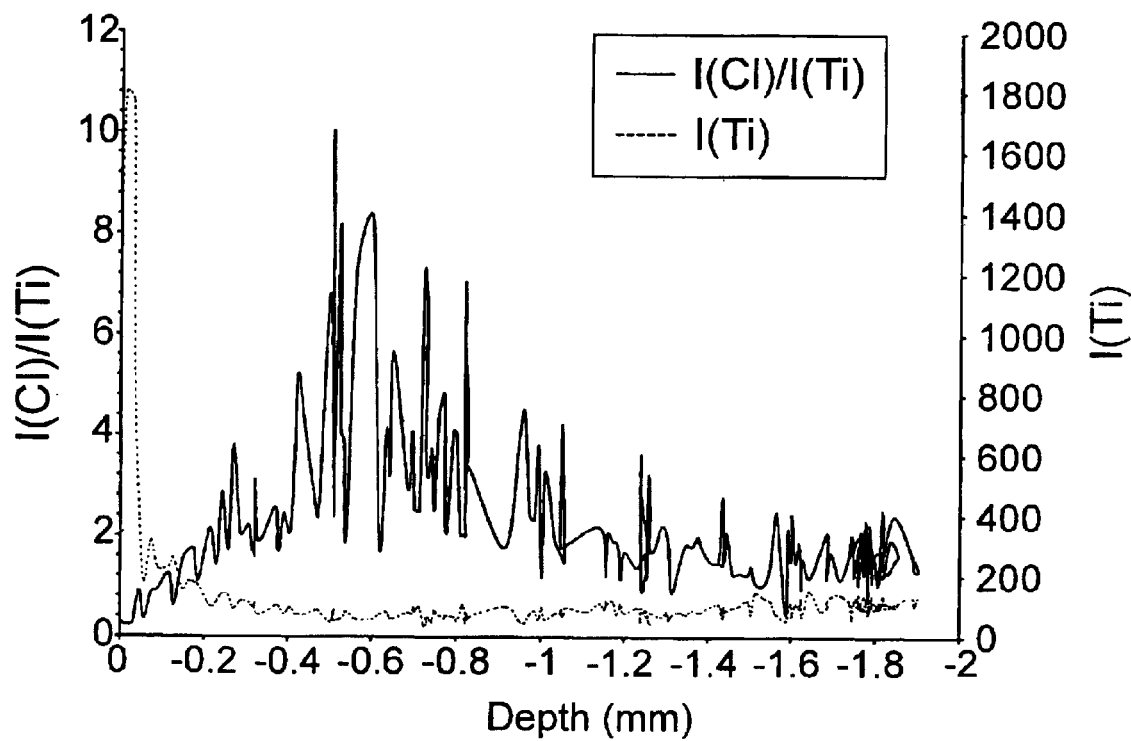
FIG. 8 shows the evolution of spectral line intensities obtained by LIPS as a function of depth.

FIG. 8 shows the full realization of the present invention, the depth information (from FIG. 7) being combined with the compositional analysis (from FIG. 5). This figure directly provides the location of various heterogeneities in the tablet. In particular, one may determine the coating thickness from the depth profile of the Ti line, namely by defining the thickness as the halfway point of the steep decay of titanium signal. This point is reached between the $4^{th}$ and $5^{th}$ laser shots. Since the depths reached after these shots were 46 and 56 $\mu$m respectively, we may then conclude that the coating is approximately 50 $\mu$m thick.

It is understood that simply repeating such a depth profile at several locations on the tablet surface can provide a three-dimensional mapping of the tablet composition. In particular, any variation of coating thickness across the tablet can be readily observed by this technique.

The above description of the present invention is susceptible to various modifications, changes and adaptations, and the same are intended to be comprehended within the scope of the appended claims.

We claim:

1. A method of compositional analysis of a heterogeneous material of one or more components, comprising:
   (a) directing a pulse of laser radiation at a target of the heterogeneous material to ablate an amount thereof, and to form an ablation crater having a depth;
   (b) determining the concentration of one or more selected components in the heterogeneous material ablated from the target;
   (c) measuring in situ the depth of the ablation crater other than in dependence upon time gated imaging data of the directed pulse of laser radiation; and
   (d) determining a composition of the heterogeneous material at the depth.

2. A method according to claim 1, wherein measuring the depth is performed based on sensing of a beam of light directed at the target and other than the pulse of laser radiation.

3. A method according to claim 1, wherein at least one of (a) to (d) is repeated for determining a compositional profile of the heterogeneous material as a function of the depth.

4. A method according to claim 3 further comprising:
   (e) shifting a target to a each of a plurality of locations across the heterogeneous material, and
   (f) repeating steps (a) to (e).

5. A method according to claim 4 comprising determining a compositional profile of the heterogeneous material in three dimensions.

6. A method according to claim 4, wherein measuring the depth of the ablation crater further comprises:
   (j) measuring the depth of the ablation crater at each of a plurality of points thereacross for each of a plurality of ablation craters; and
   (k) generating a compositional profile of the heterogeneous material in three dimensions.

7. A method according to claim 4, further comprising processing data from steps (a) to (d) to align one with another spatially for forming the compositional profile of the heterogeneous material as a function of the depth.

8. A method according to claim 3 wherein measuring the depth of the ablation crater further comprises:
   (g) measuring the depth of the ablation crater at each of a plurality of points thereacross; and
   (h) generating a depth profile of the ablation crater.

9. A method according to claim 8, further comprising:
   (h) repeating step (h) at a plurality of depths of the ablation crater; and
   (i) generating an evolution of the depth profile of the ablation crater.

10. A method according to claim 3, further comprising processing data from steps (a) to (d) to align one with another spatially for forming the compositional profile of the heterogeneous material as a function of the depth.

11. A method according to claim 1, wherein the concentration is determined by a spectrochemical analysis technique selected from a group consisting of: optical emission spectrometry of the light emitted by the plasma produced above the target concomitantly with the laser ablative event; optical emission spectrometry, following the introduction of the material ablated from the target into an auxiliary plasma discharge where said material is excited to emit light; and mass spectrometry of said material ablated from the target, following the introduction of the ablated material into said auxiliary plasma discharge, from which the ablated material is extracted in ionized form.

12. A method according to claim 1, wherein measuring the depth is performed by a technique selected from a group consisting of: confocal microscopy, laser triangulation, and interferometry using a short coherence length light source.

13. A method according to claim 12, wherein measuring the depth comprises:
   directing a beam of short coherence length light toward both the ablation crater and an interferometric mirror; and
   measuring interference between light reflected from the ablation crater and reflected from the interferometric mirror.

14. A method according to claim 13, comprising:
   directing a beam of short coherence length light toward both another location within the ablation crater and the interferometric mirror;
   measuring interference between light reflected from the other location within the ablation crater and reflected from the interferometric mirror; and
   generating a depth profile of the ablation crater.

15. A method according to claim 13 wherein the short coherence light propagates colinearly with the laser radiation.

16. A method according to claim 13 wherein the short coherence light propagates at an angle to the direction of the laser radiation.

17. A method according to claim 12, further comprising:
   directing a beam of short coherence length light toward a surface inside the ablation crater, a surface outside the ablation crater and an interferometric mirror, and
   measuring interference between light reflected from the surface inside the ablation crater and the interferometric mirror and between light reflected from the surface outside the ablation crater and the interferometric mirror.

18. An apparatus for compositional analysis of a heterogeneous material of one or more components, comprising:
   a laser source for producing an ablation beam of laser pulses of sufficient fluence to ablate an amount of the heterogeneous material from a target under study and thereby to form an ablation crater of a depth;

a spectrometric device for detecting and determining the concentration of one or more selected components in the heterogeneous material ablated from the target; and, an optical device for measuring in situ the depth of the ablation crater using other than time gated imaging.

19. An apparatus according to claim 18, wherein said optical device comprises a light source for directing light at the heterogeneous material and a sensor for sensing the light from the light source.

20. An apparatus according to claim 18, wherein said spectrometric device is selected from a group consisting of: an optical spectrometric device for a spectrochemic analysis using light emitted by plasma produced above the target concomitantly with the laser ablative event; an optical spectrometric device for a spectrochemic analysis using light emitted by an auxiliary plasma discharge into which the material ablated from the target is introduced; and a mass spectrometer for determining the concentration of one or more selected components in the material ablated from the target and subsequently ionized.

21. An apparatus according to claim 18, wherein the optical device for measuring the depth of the ablation crater is selected from a group consisting of a confocal microscopy device, a laser triangulation device, and an interferometer relying on a short coherence length light source.

22. An apparatus according to claim 18, comprising a mechanical device for scanning a beam of the optical device across the target for measuring the depth of the ablation crater.

23. An apparatus according to claim 18, comprising an actuator for effecting relative motion between the beam of the optical device and the target.

24. An apparatus according to claim 18, wherein the optical device for measuring the depth of the ablation crater comprises a dual measuring beam system for simultaneous measurement of depth at two points on the sample surface.

* * * * *